US 6,740,088 B1

United States Patent
Kozak et al.

(10) Patent No.: US 6,740,088 B1
(45) Date of Patent: May 25, 2004

(54) ANTERIOR LUMBAR PLATE AND METHOD

(75) Inventors: Jeffrey Kozak, Houston, TX (US); Bradley T. Estes, Memphis, TN (US); Lawrence M. Boyd, Durham, NC (US)

(73) Assignee: SDGI Holdings, Inc., Wilmington, DE (US)

( * ) Notice: Subject to any disclaimer, the term of this patent is extended or adjusted under 35 U.S.C. 154(b) by 218 days.

(21) Appl. No.: 09/696,130

(22) Filed: Oct. 25, 2000

(51) Int. Cl.$^7$ .................................................. A61F 2/30
(52) U.S. Cl. ............................................. 606/69; 606/61
(58) Field of Search ............................... 606/61, 69–71, 606/62

(56) References Cited

U.S. PATENT DOCUMENTS

| | | | |
|---|---|---|---|
| 4,289,123 A | 9/1981 | Dunn | |
| 5,092,893 A | 3/1992 | Smith | |
| 5,127,912 A | * 7/1992 | Ray et al. | 606/61 |
| 5,180,381 A | 1/1993 | Aust et al. | |
| 5,318,567 A | 6/1994 | Vichard | 606/65 |
| 5,364,399 A | 11/1994 | Lowery et al. | 606/60 |
| 5,397,364 A | * 3/1995 | Kozak et al. | 606/61 |
| 5,520,690 A | 5/1996 | Errico et al. | |
| 5,527,311 A | 6/1996 | Procter et al. | |
| 5,549,612 A | 8/1996 | Yapp et al. | |
| 5,603,713 A | 2/1997 | Aust et al. | |
| 5,607,426 A | 3/1997 | Ralph et al. | |
| 5,616,144 A | 4/1997 | Yapp et al. | |
| 5,634,926 A | 6/1997 | Jobe | |
| 5,766,175 A | 6/1998 | Martinotti | |
| 5,800,433 A | 9/1998 | Benzel et al. | 606/61 |
| 5,843,082 A | 12/1998 | Yuan et al. | 606/61 |
| 6,017,345 A | 1/2000 | Richelsoph | |
| 6,030,389 A | 2/2000 | Wagner et al. | |
| 6,036,693 A | 3/2000 | Yuan et al. | 606/61 |
| 6,045,552 A | * 4/2000 | Zucherman et al. | 606/61 |
| 6,139,550 A | 10/2000 | Michelson | |
| 6,183,478 B1 | 2/2001 | Konieczynski | |
| 6,280,445 B1 | 8/2001 | Morrison et al. | |
| 6,315,779 B1 | 11/2001 | Morrison et al. | |
| 6,331,179 B1 | 12/2001 | Freid et al. | |
| 6,383,186 B1 | 5/2002 | Michelson | |
| 6,416,528 B1 | 7/2002 | Michelson | |
| 6,454,769 B2 | 9/2002 | Wagner et al. | |
| 6,565,571 B1 | 5/2003 | Jackowski et al. | |
| 6,592,586 B1 | 7/2003 | Michelson | |
| 6,599,290 B2 | 7/2003 | Bailey et al. | |
| 6,605,090 B1 | 8/2003 | Trieu et al. | |
| 6,620,163 B1 | 9/2003 | Michelson | |

* cited by examiner

*Primary Examiner*—Michael Peffley
*Assistant Examiner*—Peter J Vrettakos
(74) *Attorney, Agent, or Firm*—Woodard, Emhardt, Moriarty, McNett & Henry LLP

(57) ABSTRACT

A plate of biocompatible material is provided having curvature in two planes such that it conforms to the curvature of the L5 vertebral body and to the patient's lordotic curve. Holes are provided receiving screws for anchorage in the vertebral body and sacrum. A flange or foot portion on the plate provides a wider base end area for support in the L5-S1 interspace. The foot portion is also arranged for appropriate entry angle of screws into the sacrum such as to improve anchorage in the sacrum. Anti-backout and low profile features are incorporated. The anterior lumbar plate is situated to maintain the anterior interbody bone graft in compression by resisting tensile forces during extension.

13 Claims, 5 Drawing Sheets

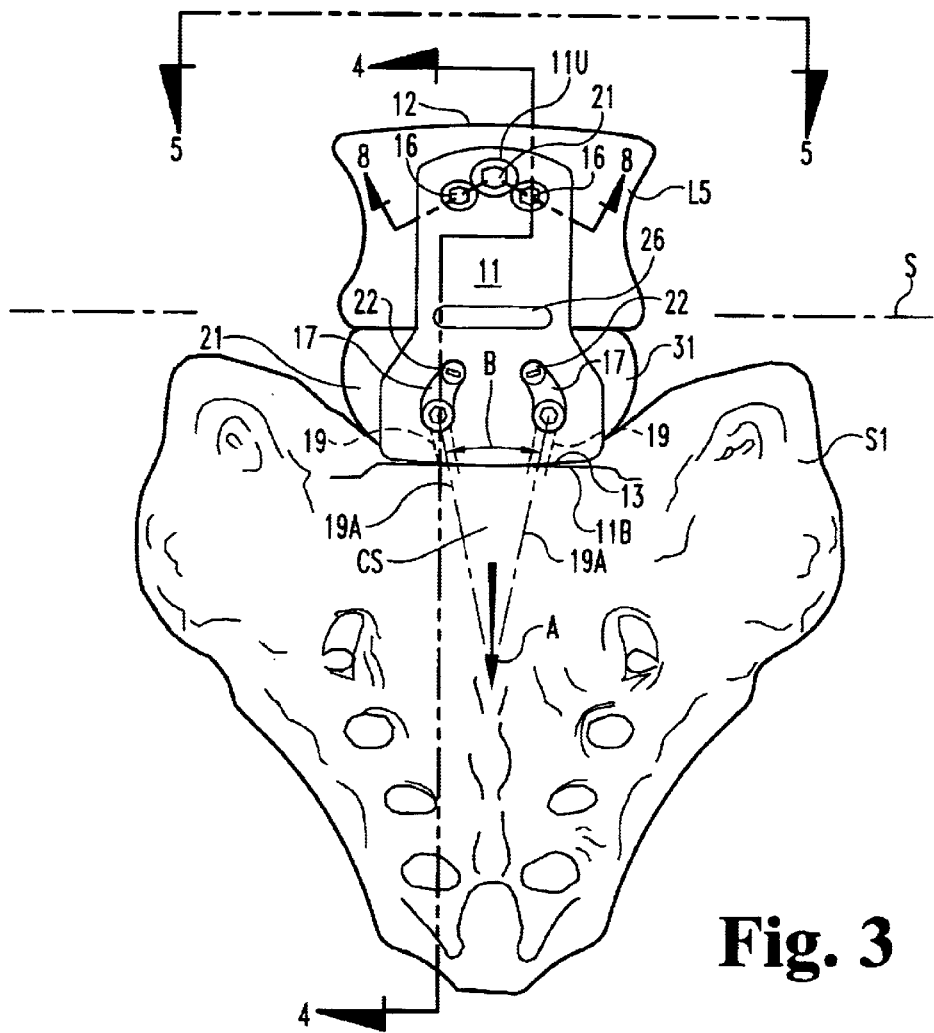
Fig. 3
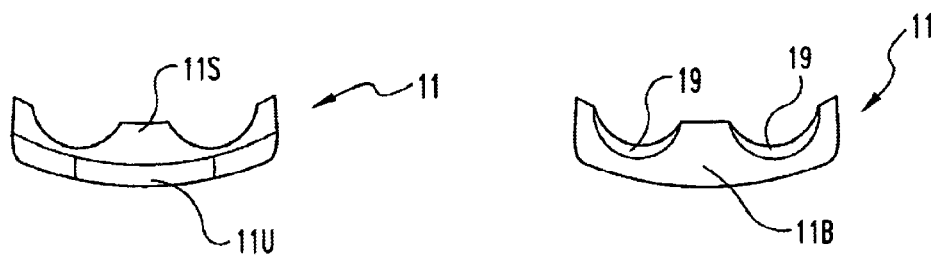
Fig. 5  Fig. 6

ANTERIOR LUMBAR PLATE AND METHOD

BACKGROUND OF THE INVENTION

1. Field of the Invention

This invention relates generally to spinal fixation systems, and more particularly to a plate to immobilize the L5 vertebra with respect to the S1 vertebra.

2. Description of Prior Art

Various types of plating devices and systems, have been used to stabilize portions of the spine. For cases in which interbody fusion is desired in the lumbar-sacral region, stabilization using plating has been preferred by many surgeons for good fixation and to avoid damage to the vascular and nervous system components adjacent the anterior surfaces of the L5 vertebra. A plating system for stabilization of the L5-S1 junction is disclosed in U.S. Pat. No. 5,127,912 issued Jul. 7, 1992 to Ray and Ashman. It is a posterior system. While posterior fixation systems are often used in anterior/posterior fusions, the anterior surgical approach to the fusion is preferred from several perspectives. Less blood loss and reduced post-operative pain can be achieved. Also, effective anterior plating could avoid the additional posterior surgery necessary in the past to provide the additional stabilization needed to establish a reasonable fusion rate.

U.S. Pat. No. 6,045,552 issued Apr. 4, 2000 to Zucherman and Hsu discloses a plate for immobilizing the L5 vertebra with respect to the S1 vertebra. Earlier patents and publications are cited in that patent. Also, it is understood that Kostuick and Yuan had modified anterio-lateral plates, for example (e.g., the Syracuse I Plate) for use on the anterior lumbar spine. Also, it is understood that earlier literature reported clinical experience (Humphries and Hawk 1951, 1961) with an anterior lumbar plate manufactured by Austenal Company, New York. There remains a need for additional stability to an anterior lumbar interbody fusion using the same anterior surgical site for plating.

SUMMARY OF THE INVENTION

Described briefly according to the illustrated embodiment of the invention, a plate is provided having curvature in two planes such that it conforms to the curvature of the L5 vertebral body and the patient's lordotic curve. Holes are provided receiving screws for anchorage in the vertebral body and sacrum. The screws and receiver holes in an upper portion of the plate are generally perpendicular to that portion of the plate. A lower portion of the plate is formed with a flange or foot portion which provides a wider base end area for support on the upper face of S1 in the L5-S1 interspace. The foot portion is also arranged for appropriate entry angle of screws into the sacrum such as to improve anchorage in the sacrum. The screws and receiver holes in the lower portion of the plate are through the front and bottom walls of the lower portion of the plate and at a steep angle relative to the front of the plate and engaged with the cortical bone of the sacrum at the superior end plate and at the S1-S2 junction. The foot portion also incorporates anti-backout and low profile features. The anterior lumbar plate is situated to maintain the anterior interbody bone graft in compression by resisting tensile forces during extension. The plate can also be extended to the L4-L5 junction by increasing the length of the plate and inclusion of holes in the upper portion for anchoring to L4.

BRIEF DESCRIPTION OF THE DRAWINGS

FIG. 3 is an anterior view of the plate of FIGS. 1 and 2 fixed at the L5-S1 junction.

FIG. 5 is a top plan view of the anterior lumbar plate.

FIG. 6 is a bottom plan view of the plate.

DESCRIPTION OF THE ILLUSTRATED EMBODIMENT

Figure 1:
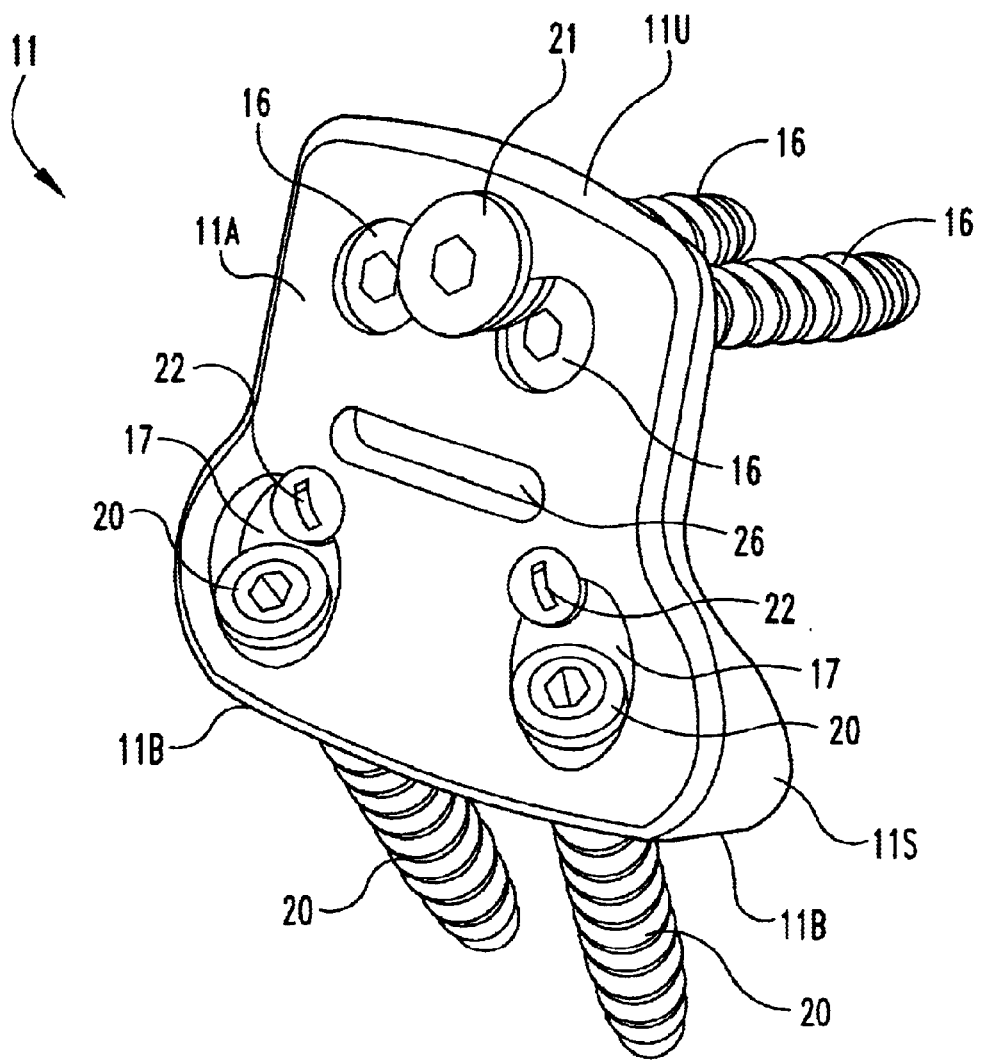
FIG. 1 is a perspective view of an anterior lumbar plate assembly according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
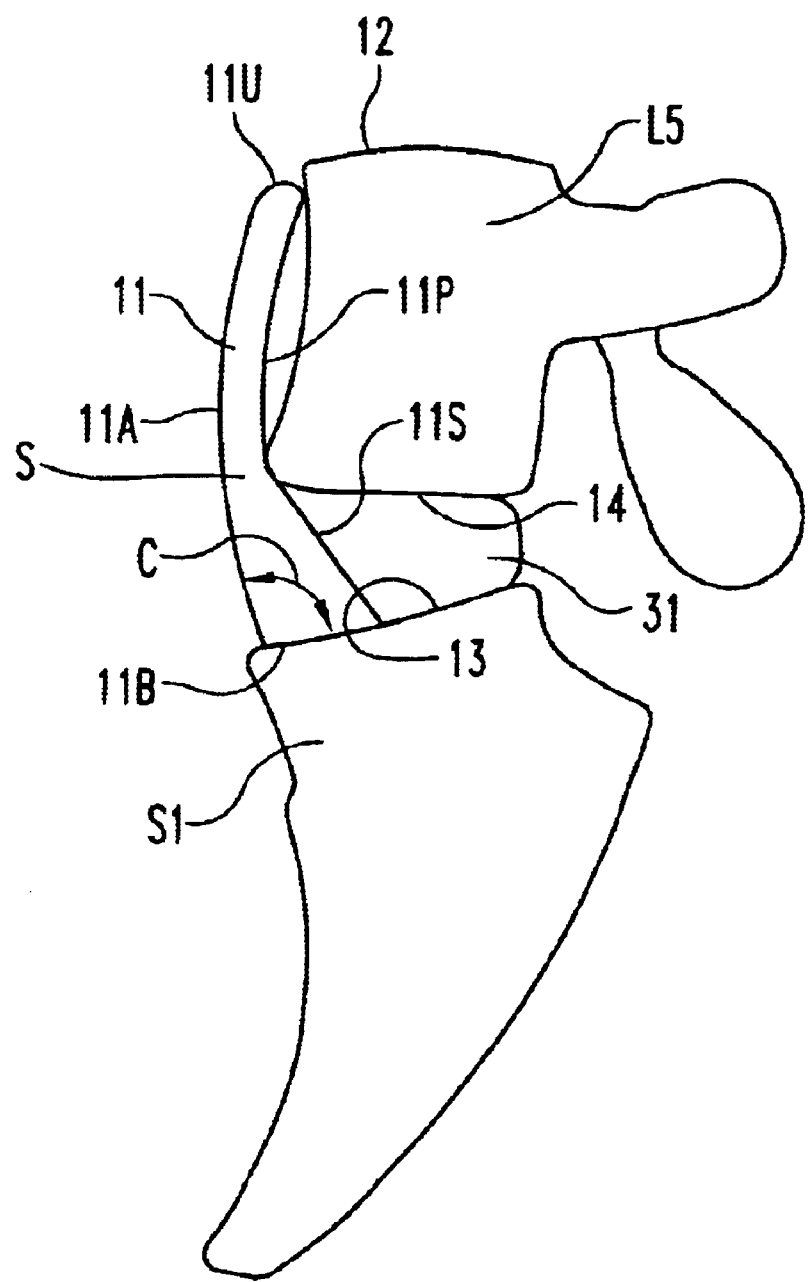
FIG. 2 is a side elevational view of the plate fixed at the L5-S1 junction of the lumbar/sacral region shown schematically.
Figures 4, 4A:
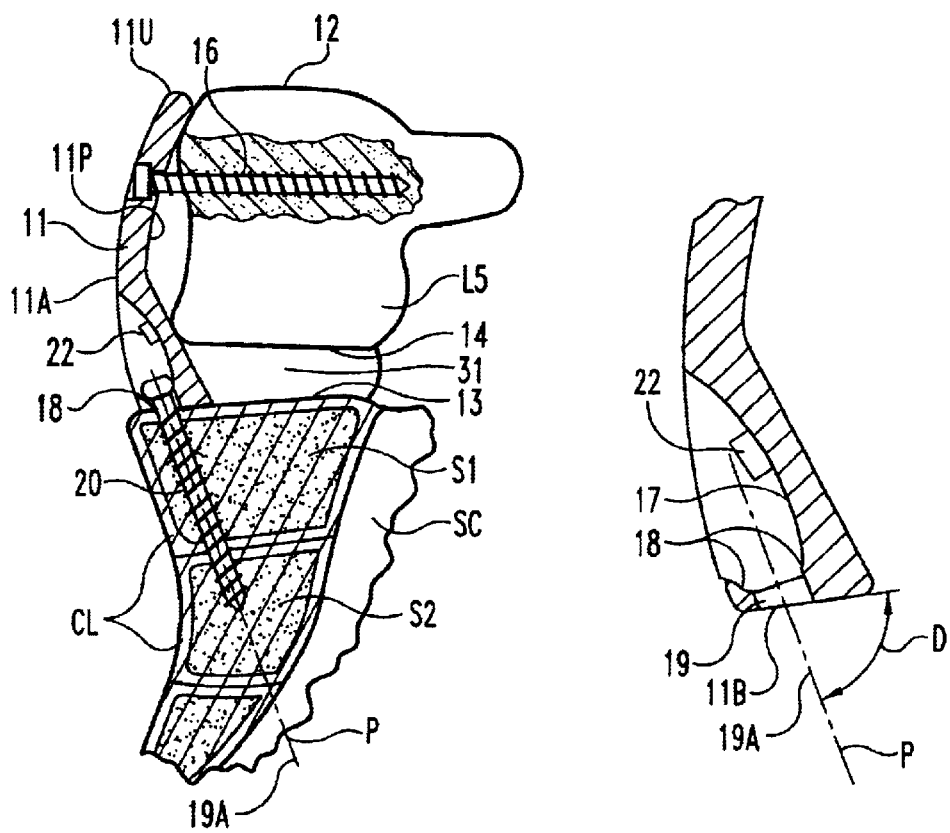
FIG. 4 is a sectional view taken at line 4—4 in FIG. 3 and viewed in the direction of the arrows and showing the plate fixed to L5 and S1, S2, shown schematically and fragmentarily.
FIG. 4A is an enlarged fragment of FIG. 4.

The anterior lumbar plate 11 according to the illustrated embodiment of the invention is generally pear-shaped as viewed from the front in FIG. 3 to reduce contact with great vessels, but is curved in a vertical plane as shown in FIGS. 2 and 4, and is curved in a horizontal plane as shown in FIGS. 5 and 6. This facilitates fitting around the vertebra L5 and enables the anterior face 11A (FIGS. 2 and 4) to smoothly follow the curvature of S1 and the spinal column above it. The upper portion 11P of the posterior face follows the same curves but changes at the foot portion 11S so it can partially enter the intradiscal space between L5 and S1. It is preferable that the upper end 11U of the plate be slightly lower than the top surface 12 of L5. The lower face 11B of the foot portion 11S of plate 11 is intended to be located at or immediately above the superior plate face 13 of S1.

Depending upon the anatomy of the patient, the overall height between the bottom face 11B and top edge 11U of the plate is likely to be between 4.0 centimeters and 5.4 centimeters with an average of about 4.5 centimeters. The overall width may be about 2.8 centimeters at the narrow portion and about 4.0 centimeters at the foot portion. The depth (thickness) between front and rear faces of the upper portion of the plate is about 5 millimeters and increases from slot 26 down to a maximum of about 9 millimeters at the face 11B. As mentioned above, if it is desired to extend the plate to stabilize two levels, that can be simply done by increasing the overall height between the bottom face 11B of the plate and the top edge of the plate and adding screw holes of the type discussed below to anchor into the L4 vertebra.

As shown in FIGS. 3 and 4, there are two screw holes in the upper portion of the plate and which receive screws 16 which are screwed into L5. The foot portion of the plate has two recesses 17 with lower wall portions 18 curving inwardly FIG. 4A and providing screw guide entrances to holes 19 which extend from there through the bottom face 11B. Screws 20 are received downward through holes 19 and screwed into and through both cortical bone at the superior end plate and cancellous bone of S1, and through cortical bone of both vertebral segments at the junction S1-S2. As an example, the screws may be 6.5 mm diameter cancellous bone screws. The screw hole axes 19A are also oriented from the screw entry surface of recesses 17 toward the longitudinal axis A of the plate which is usually substantially co-planar with the mid-plane of the spine. The trajectory for screws 20 and resulting angle B and the angle D (FIG. 4A) of the plane P relative to the plane of the plate bottom 11B, are determined by the surgeon using direct visual and X-ray fluoroscopy of the sacrum. It is expected that the included angle (B) is likely to be between 10 and 30 degrees if measured in a plane P of the screw axes (FIG. 4) or a plane close to the screw axes if they are not co-planar. The underside of the heads of screws 20 are preferably rounded above the smooth shank portions of the screws received in the holes 19, so that the screw heads can become well seated in the curved seating surface 18 by permitting some angulation of the screws relative to the plate 11 as the screws are installed in the sacrum and tightened in place.

Anti-backout means are provided. In the illustrated example, an anti-backout screw 21 (FIG. 3) is screwed into the plate and extends over the heads of the two screws 16 to prevent them from backing out of the bone L5. Screw 21 may be of the nature shown in U.S. Pat. No. 5,364,399 to Lowery et al. Alternatives are possible. One example is an interlocking wedge feature of anti-backout screw and bone screws to prevent them from backing out. In that connection, and referring to FIG. 8, which is a section taken at line 8—8 in FIG. 3 and viewed in the direction of the arrows, in this instance, the particular screws are bone screws 16A which are anchored in the vertebral body and seat on the screw shoulders 11S of plate 11 and anchor the plate 11 to the vertebral body L5. The anti-backout screw 21 is threaded into the plate 11 at the inter-engaging threads 21T. The angled heads of these screws as shown at 16H for screws 16A and 21H for the anti-backout screw 21, act as male and female Morse tapers. The holes in plate 11 are counter-sunk at the diameter of the largest part of the head of the bone screw (i.e. at the bottom of the head). The set screw 21 is placed in the threaded aperture between the bone screws in position to mate with the heads of the bone screws. The countersink bottom surface 11S may be at the same depth for all three screws.

Figure 8:
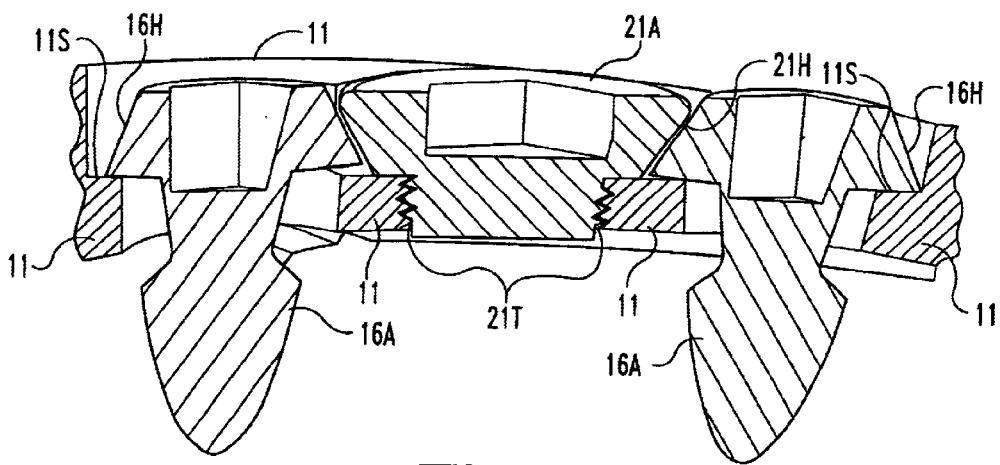
FIG. 8 is a fragmentary sectional view through a portion of the plate 11 at line 8—8 in FIG. 3 and viewed in the direction of the arrows.

The set screw arrangement can be used regardless of whether the screws 16 or 16A are rigid or semi-rigid. If the geometry of the plate 11 is such that the set screw 21 seats rigidly against the heads of screw 16, it is considered a rigid construct. If, however, a gap is left between the underneath side of the set screw 21, and the top of the bone screws, the bone screws are semi-rigid, allowing motion superiorly and inferiorly, effectively allowing subsidence of the interbody graft. In the example of FIG. 8, the set screw 21A is seated on the top of 11S of the countersink (counter-bore) in the plate, and allows some gap between its Morse tapered face 21H and the matable Morse tapered faces 16H of the bone screws. But in the event of any tendency of the bone screw to back out, the wedging between those surfaces will take place and terminate any back-out. This arrangement of the interlocking taper between the two bone screws and the anti-backout screw can be expanded in a way such that the anti-backout screw is centered in an array of four bone screws.

Figure 7:
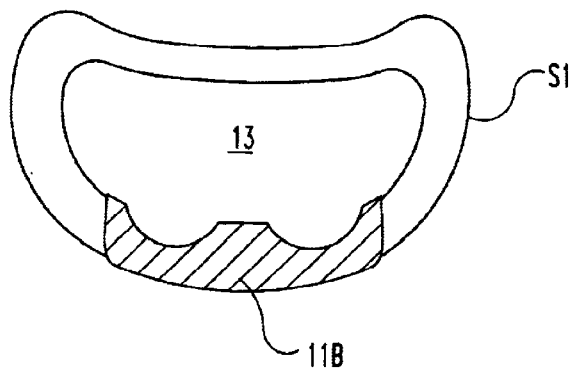
FIG. 7 is a schematic illustration of the load bearing of the plate on the ring apophysis of the sacrum.

Referring now to FIG. 7, there is shown the shape 11B of the bottom of plate 11 superimposed on the ring apophysis of the sacrum S1, demonstrating the plate 11 load-bearing on the strong ring apophysis for improved long-term fixation.

Anti-backout screws 22 are provided in the recesses 17 and positioned to prevent the screws 20 from backing out of the S1 bone. Other anti-backout approaches may be used. Another example is a nickel-titanium, shape memory alloy collar arrangement as disclosed in U.S. Pat. No. 5,578,034 to Estes. The near-vertical orientation of the screws 20 relative to the plate face 11B, and thereby to the superior end plate surface of S1, enables screw anchorage in dense cortical bone at the sacral promontory and at the S1-S2 junction without risk of the screws entering the sacral canal SC. In addition, the orientation of the axes of the two screws 20 at an angle B (FIG. 3) assists in the anti-backout or pull-out feature of this invention as it traps a wedge of cancellous bone at CS between the two screws 20, and which is very resistant to being pulled out.

As shown in FIGS. 2 and 4, the bottom plate face 11B of the wedge or foot portion of the plate 11 is at approximately 90 degrees (angle C) with the anterior face of the plate 11. Depending upon the normal angle between the superior end plate of S1 and the inferior end plate surface of L5 as well as can be determined for a patient, the end plate angle C of the plate furnished for the procedure might be selected from 80 to 100 degrees.

In addition to appropriately choosing a size of plate to fit the patient, a plate formation assistance feature is provided. In the illustrated embodiment of the plate, this is a slot 26. This slot is about 3 millimeters wide, 18 millimeters long and located about midway between the upper end 11U and lower end 11B of the plate. The location is intended to help the surgeon appropriately bend the plate about an axis S (FIGS. 2 and 3) perpendicular to the mid-plane and located immediately below the level of the lower surface 14 of L5. This facilitates the bending deemed necessary by the surgeon to best fit the plate 11 to L5 and to S1 with the foot portion 11S extending somewhat into the anterior portion of the disc space. This is to avoid necessitating resection of some of the lower anterior portion of L5 to receive the upper portion 11A of the plate as could occur if the bend were too low and, if the bend were too high, having the anterior surface of the plate at the bend projecting too far out in the anterior direction with attendant risk of impingement of the vasculature structures and sympathetic nerve bundle.

As it is possible to encounter in different patients, a range of space between the superior plate surface 13 of S1 and inferior plate surface 14 of L5, anywhere from 12 to 18 or so millimeters at the anterior edges, it can be desirable to provide a selection of several sizes of plates and locations of the relief slots, to provide the optimum choices for the spinal surgeon. As mentioned above, if it is desirable to provide fusion at more than just the one vertebral space described, the plate can be made taller to cover an additional one or more intervertebral junctions, with screws such as 16 installed in L4 and such higher vertebrae as are associated with the fusion junctions.

An example of material which may be employed in the use of the invention is a T1 6Al-4V titanium alloy according to Standard ASTM F-136. This may be associated with various types of interbody fusion device or devices and bone graft materials 31. Examples are shown and described in U.S. Pat. No. 5,397,364 to Kozak and Boyd. Of course, the present invention may be used with other types of materials, surface finishes, and interbody fusion devices of bone dowel, push-in cage, screw-in cage, with bone graft and/or graft substitute material or other types of devices suitable for such fusion applications. The anterior surface is very smooth with rounded edges to avoid damage to the vascular and nervous systems.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A stabilizer for lumbar/sacral junction and comprising:

a plate having a front wall and a foot portion projecting rearwardly from a lower portion of the wall and having a caudally-directed bottom surface;

two upper holes in the wall to receive screws for passage into an L5 vertebra; and two lower holes in the wall and extending through the bottom surface of the plate to receive screws for passage through said foot portion into the sacrum.

2. The stabilizer of claim 1 and wherein:

said plate has front wall recesses, one for each of said lower holes and providing seating surfaces for heads of screws when received in said lower holes.

3. The stabilizer of claim 2 and wherein:

said seating surfaces are inclined inwardly whereby screw heads when received thereon are self-centering.

4. The stabilizer of claim 3 and wherein:

said inwardly inclined surfaces are curved downwardly toward entrance ends of said lower holes.

5. The stabilizer of claim 3 and wherein:

said lower holes have axes which converge as they extend below the bottom of the plate.

6. The stabilizer of claim 5 and wherein:

said axes lie in a plane generally parallel to the lower portion of the front wall.

7. A stabilizer for the lumbar/sacral joint of a higher vertebrate and comprising:

a plate having an upper portion and a foot portion, the upper portion being curved in a horizontal plane for fitting to an L5 vertebra and the foot portion being shaped to reside in anterior inter-vertebral space between L5 and S1 and to be fittingly received and rest on the sacrum superior end plate;

at least one fastener through the upper portion and generally perpendicular to the upper portion for anchorage to L5;

a second fastener through the foot portion at an angle for reception and extension in cortical bone of the sacrum at the sacral promontory, and for engagement in cortical bone at the S1-S2 junction.

8. The stabilizer of claim 7 and further comprising:

third and fourth fasteners, said third fastener extending through the upper portion and generally perpendicular to the upper portion;

said fourth fastener extending through said foot portion at an angle for reception and extension in cortical bone of the sacrum at the sacral promontory and for engagement in cortical bone at the S1-S2 junction.

9. The stabilizer of claim 8 and wherein:

said second and fourth fasteners are elongate and have longitudinal axes and are oriented with their axes converging from their respective points of departure downward from a bottom surface of said foot portion.

10. The stabilizer of claim 7 and wherein:

said foot portion has a front wall and a bottom wall; and said foot portion has an aperture therethrough having a fastener entrance through said front wall and a fastener exit through said bottom wall.

11. The stabilizer of claim 10 and wherein:

said aperture has a portion intermediate said entrance and exit, and a curved, fastener-head seating surface converging from said front wall to said intermediate portion.

12. The stabilizer of claim 10 and wherein:

said plate is made of a biocompatible alloy, and said foot portion thereof is adapted to load bearing on ring apophysis of the sacrum, the upper portion and foot portion being shaped in an anterior aspect to minimize contact with great circulatory vessels in the region of L5-S1.

13. The stabilizer of claim 1 wherein said lower holes have axes which converge as they extend below the bottom of the plate.

* * * * *